(12) United States Patent
Deluca (10) Patent No.: US 10,391,028 B2
(45) Date of Patent: Aug. 27, 2019

(54) SECURE PILL CONTAINER

(71) Applicant: Theresa Gloria Deluca, Baltimore, MD (US)

(72) Inventor: Theresa Gloria Deluca, Baltimore, MD (US)

(*) Notice: Subject to any disclaimer, the term of this patent is extended or adjusted under 35 U.S.C. 154(b) by 0 days.

(21) Appl. No.: 15/957,156

(22) Filed: Apr. 19, 2018

(65) Prior Publication Data

US 2018/0303709 A1 Oct. 25, 2018

Related U.S. Application Data

(60) Provisional application No. 62/487,279, filed on Apr. 19, 2017.

(51) Int. Cl.
| | | |
|---|---|---|
| *A61J 1/03* | (2006.01) | |
| *A61J 7/00* | (2006.01) | |
| *G07C 9/00* | (2006.01) | |
| *A61B 5/1174* | (2016.01) | |
| *B65D 83/04* | (2006.01) | |
| *A61J 7/04* | (2006.01) | |
| *A61B 5/1172* | (2016.01) | |
| *B65D 55/02* | (2006.01) | |
| *A61B 5/1171* | (2016.01) | |

(52) U.S. Cl.
CPC .............. *A61J 1/03* (2013.01); *A61B 5/1172* (2013.01); *A61B 5/1174* (2013.01); *A61J 7/0084* (2013.01); *A61J 7/0445* (2015.05); *A61J 7/0463* (2015.05); *A61J 7/0481* (2013.01); *B65D 83/04* (2013.01); *G07C 9/00896* (2013.01); *A61B 5/1176* (2013.01); *B65D 55/02* (2013.01); *B65D 2215/00* (2013.01)

(58) Field of Classification Search
CPC .......... A61J 1/03; A61J 7/0084; A61J 7/0481; A61J 7/0463; A61J 7/0445; A61B 5/1174; A61B 5/1172; A61B 5/1176; B65D 83/04; B65D 55/02; B65D 2215/00; G07C 9/00896
USPC .................................................. 700/231–244
See application file for complete search history.

(56) References Cited

U.S. PATENT DOCUMENTS

| | | | |
|---|---|---|---|
| 5,850,937 A | 12/1998 | Rauche | |
| 5,954,225 A | 9/1999 | Powe | |
| 6,116,461 A * | 9/2000 | Broadfield | ........... A61G 12/001 |
| | | | 206/443 |
| 6,169,707 B1 | 1/2001 | Newland | |

(Continued)

OTHER PUBLICATIONS

Donna J. HARDINSECURE Enhanced Pill ContainerDec. 11, 2010.

(Continued)

*Primary Examiner* — Michael Collins
(74) *Attorney, Agent, or Firm* — Global Intellectual Property Agency, LLC; Daniel Boudwin (57) ABSTRACT

The present invention provides a secure pharmaceutical container. The secure container includes a plurality of compartments for storing pills, tablets, solutions, pastes, creams, ointments, gels, emulsions, or any other pharmaceutical product. The compartments each include a locking mechanism that is operably connected to a biometric system, such as a fingerprint scanner. The compartments become unlocked upon the fingerprint scanner reading an approved fingerprint, ensuring that only individuals approved to have access to the container are granted access.

11 Claims, 6 Drawing Sheets

(56) References Cited

U.S. PATENT DOCUMENTS

| | | | |
|---|---|---|---|
| 6,338,007 B1* | 1/2002 | Broadfield | A61G 12/001 221/123 |
| 7,344,047 B2 | 3/2008 | Gilmore | |
| 7,359,765 B2 | 4/2008 | Varvarelis et al. | |
| 8,558,659 B2* | 10/2013 | Ross | G06F 19/3462 340/5.1 |
| 2004/0108795 A1* | 6/2004 | Meek, Jr. | E05B 47/0002 312/218 |
| 2005/0188213 A1 | 8/2005 | Xu | |
| 2005/0209733 A1 | 9/2005 | Gilmore | |
| 2006/0071011 A1 | 4/2006 | Varvarelis et al. | |
| 2006/0106491 A1 | 5/2006 | Kayner | |
| 2007/0093935 A1 | 4/2007 | Fu | |
| 2007/0188303 A1 | 8/2007 | Faro et al. | |
| 2009/0223990 A1 | 9/2009 | Bailey et al. | |
| 2009/0223994 A1 | 9/2009 | Getz | |
| 2011/0030034 A1* | 2/2011 | Ross | G06F 19/3462 726/4 |
| 2013/0197693 A1 | 8/2013 | Kamen et al. | |
| 2014/0339428 A1 | 11/2014 | O'Brien et al. | |

OTHER PUBLICATIONS

Secure Enhanced Pill Container BrochureIRI Product #3189867/16/2010.

Sellidea.comSECURE Enhanced Pill ContainerDec. 10, 2010.

\* cited by examiner

SECURE PILL CONTAINER

CROSS REFERENCE TO RELATED APPLICATIONS

This application claims priority under 35 U.S.C. § 119(e) to U.S. Provisional Application No. 62/487,279 filed on Apr. 19, 2017. The above identified patent application is incorporated by reference herein in its entirety to provide continuity of disclosure.

BACKGROUND OF THE INVENTION

Pharmaceutical products can be stored in a variety of containers, such as a medication bottle or a daily reminder container. Most medication containers do not provide security, and can be accessed by anyone, including individuals for whom the medication is not intended or prescribed. When unsecured containers are used to store medication, the medication can be stolen or misused. Not only can this be highly dangerous, but patients can also incur extra financial costs to replace the missing pills.

Therefore, there is a need in the art for a secure pharmaceutical container that provides access to medication only upon verification of an individual's identity. The present invention addresses this unmet need.

FIELD OF THE INVENTION

The present invention relates to a secure pharmaceutical container and related system that uses one or more biometric identifiers to validate the identity of an individual, as part of an approach that grants access to the container to one or more authorized individuals and denies access to the container to one or more non-authorized individuals. More specifically, the present invention provides a fingerprint-based authentication system, operably linked to a secure pharmaceutical container, to grant and deny access to the container to authorized and non-authorized individuals, respectively. A variety of pharmaceutical products, in a variety of physical forms or packaging, may be securely stored by the secure pharmaceutical container and related system.

Devices have been disclosed in the art that relate to securing medication. These include devices that have been patented and published in patent application publications. In view of the devices disclosed in the art, it is submitted that there is a need in the art for an improvement to existing medication-securing devices. In view of the present disclosure, it is submitted that the present invention substantially diverges in structural and functional elements from devices in the art, and the instant invention substantially fulfills an unmet need in the art.

SUMMARY OF THE INVENTION

In view of the disadvantages inherent in the known types of pharmaceutical securing devices in the art, the present invention provides a new and improved secured pharmaceutical container and related system, wherein the same can be utilized for providing convenience to the user when securely storing and accessing substances, such as pills, solutions, and other substances such as medications or supplements.

It is therefore an object of the present invention to provide a new and improved secured pharmaceutical container.

It is another object of the present invention to provide a new and improved secured pharmaceutical container system.

Another object of the present invention is to provide means for verifying the identity of an individual seeking access to the pharmaceutical substance(s) secured in the container or container system, using one or more biometric measurements obtained from the individual.

Yet another object of the present invention is to provide a new and improved secured pharmaceutical container or secured pharmaceutical container system that may be used by more than one individual.

Another object of the present invention is to provide a secured pharmaceutical container that may be readily manufactured from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of the invention will be particularly pointed out in the claims, the invention itself and manners in which it may be made and used may be better understood after a review of the following description, taken in connection with the accompanying drawings, wherein like numeral annotations are provided throughout.

DETAILED DESCRIPTION OF THE INVENTION

Reference is made herein to the attached drawings. Like reference numerals are used throughout the drawings to depict like or similar elements of the secure pharmaceutical container and related system. For the purposes of presenting a brief and clear description of the present invention, an exemplary embodiment will be discussed as used for securely storing one or more pharmaceuticals, such as one or more pills, tablets, or capsules. The figures are intended for representative purposes only and should not be construed to be limiting in any respect.

Figure 1:
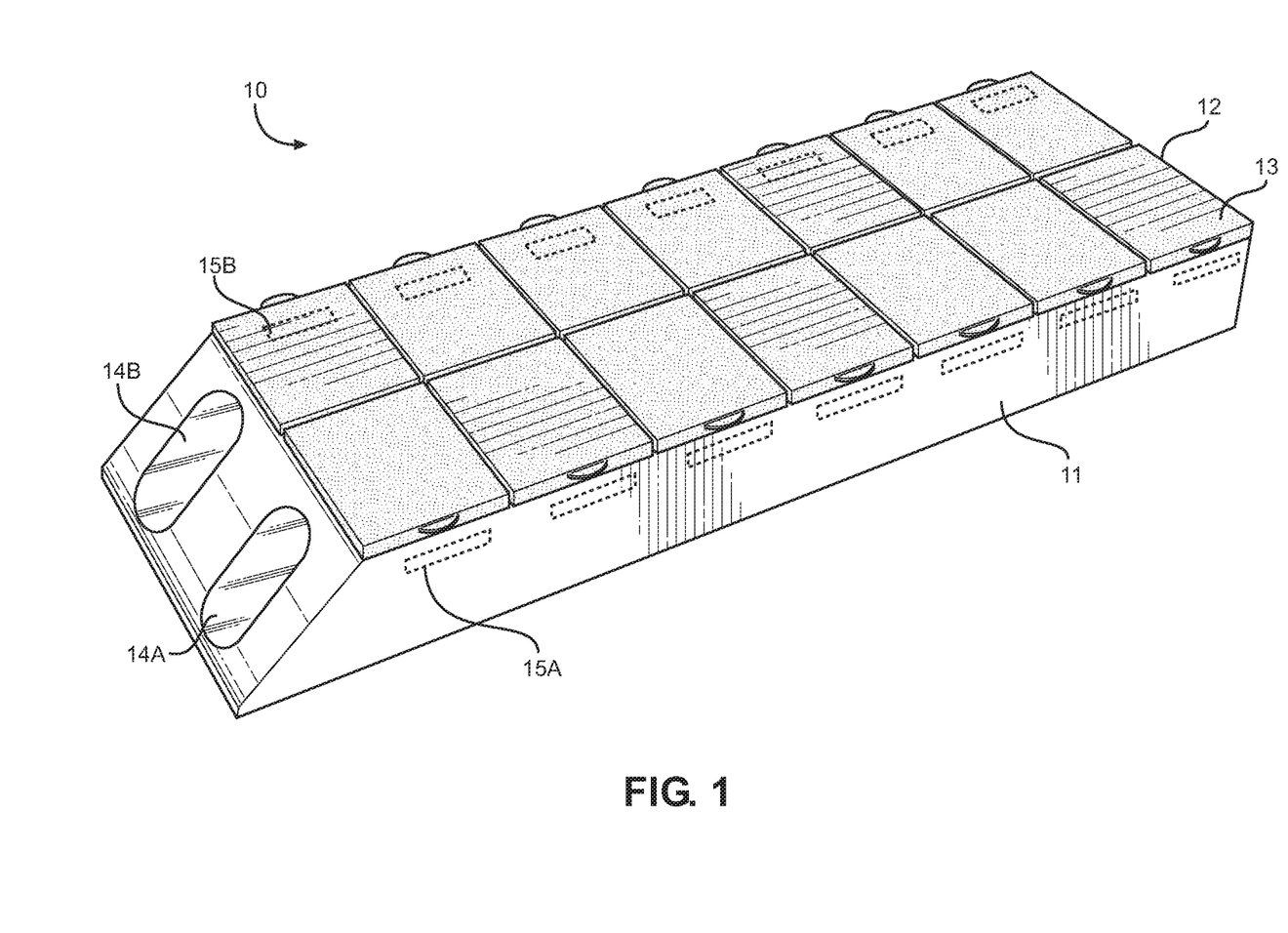
FIG. 1 shows a perspective view of the secure pill container.

Referring now to FIG. 1, there is shown a perspective view of an exemplary secure pill container. The secure pill container 10 comprises a housing 11 having a plurality of compartments 12 therein. Each compartment 12 includes a hinged lid 13 attached thereto. The lids 13 may include indicia that includes dates, names of days of the week, or other reminder mechanisms or information thereon. Further, each compartment 12 includes a locking mechanism 15a, 15b operably connected to a biometric system, such as a fingerprint scanner 14a, 14b disposed on the housing 11. In the shown embodiment, the secure pill container 10 has two fingerprint scanners 14a, 14b, each located on the housing 11 and adjacent to a row of seven locked compartments 12. The fingerprint scanner side of the housing 11 is angled to facilitate access by the user.

In one aspect, the invention provides a secure pharmaceutical container 10, comprising: a housing 11 comprising a first group of compartments wherein each compartment 12 comprises an opening that engages with a lid 13 secured in a closed position by a first locking mechanism 15a, and a second group of compartments wherein each compartment 12 comprises an opening that engages with a lid 13 secured in a closed position by a second locking mechanism 15b; and an electronic computing system comprising a non-transitory computer readable medium, a first biometric system 14a operably connected to the first locking mechanism 15a and configured to actuate the first locking mechanism, and a second biometric system 14b operably connected to the second locking mechanism 15b and configured to actuate the second locking mechanism.

In one embodiment of the secure pharmaceutical container, the housing and the electronic computing system of the secure pharmaceutical container are physically connected. For example, the electronic computing system is embedded within the housing. In one embodiment, the housing is physically connected to the electronic computing system by way of a separable physical connection, such as a wired connection.

In the shown embodiment of the secure pharmaceutical container, the first group of compartments are arranged linearly in a first row, and the second group of compartments are arranged linearly in a second row. In one embodiment, the first group comprises seven compartments. In one embodiment, the second group comprises seven compartments. In one embodiment, the first group comprises seven compartments and the second group comprise seven compartments. As shown, the first row and the second row are parallel to each other, and the openings and the lids are all on one side of the housing. In one embodiment, the openings are accessible from the perimeter of the housing.

Figure 2A:
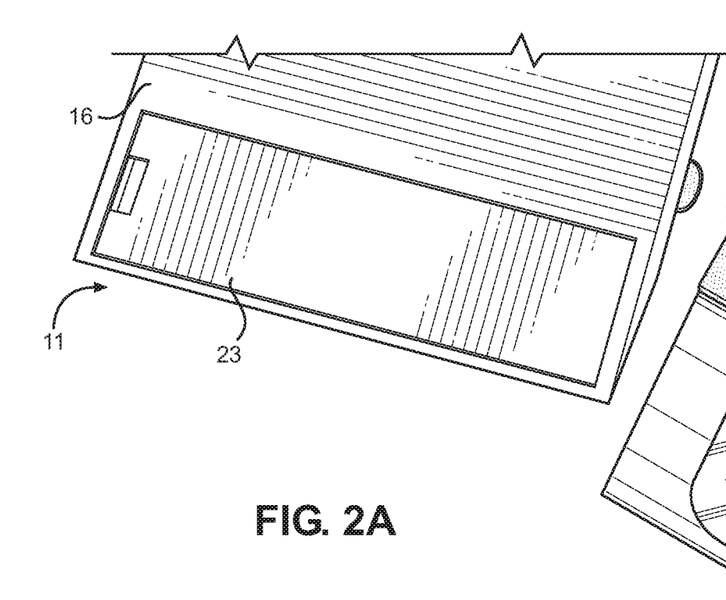
FIG. 2a shows a perspective bottom view of the fingerprint scanner of the secure pill container.
Figure 2B:
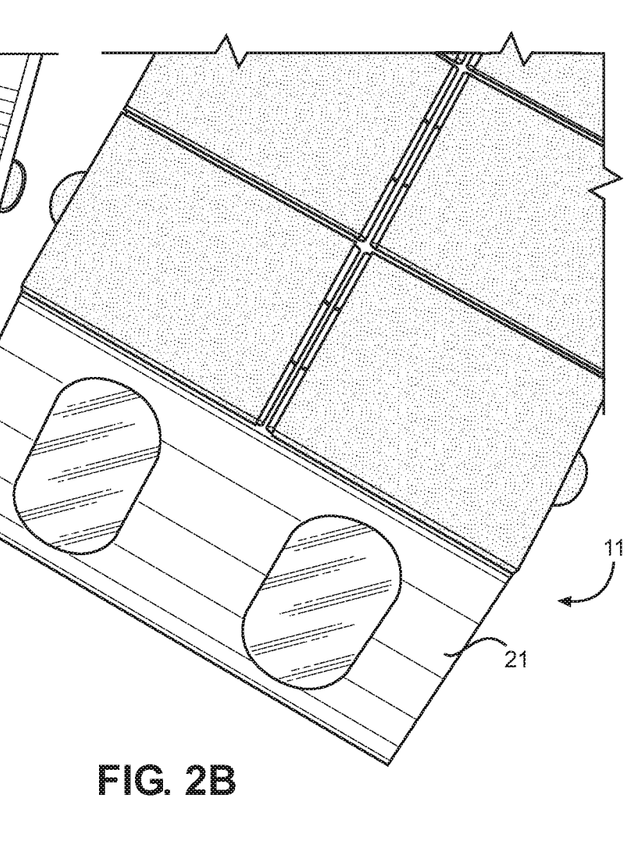
FIG. 2b shows a perspective top view of the fingerprint scanner of the secure pill container.

Referring now to FIGS. 2A and 2B, there is shown a perspective bottom and top view of the fingerprint scanners of the secure pill container, respectively. The bottom 16 of the housing 11 may include an opening secured in the closed position by a lid 23, into which a power supply, such as one or more batteries, may be placed to power operation of the fingerprint scanners 14a, 14b and locking mechanisms.

In one embodiment of the secure pharmaceutical container, the first surface and the second surface are adjacent and parallel to each other, and the first surface and the second surface are each part of an angled side 21 of the housing 11. In one embodiment, the angled side 21 of the housing 11 is angled relative to the bottom 16 of the secure pharmaceutical container 10. In one embodiment, the angle between the angled side 21 and the bottom 16 of the secure pharmaceutical container is between ten degrees and eighty degrees. In one embodiment, the angle between the angled side 21 and the bottom 16 of the secure pharmaceutical container is between twenty-five degrees and sixty-five degrees. In one embodiment, the angle between the angled side 21 and the bottom 16 of the secure pharmaceutical container is forty-five degrees.

Figure 3:
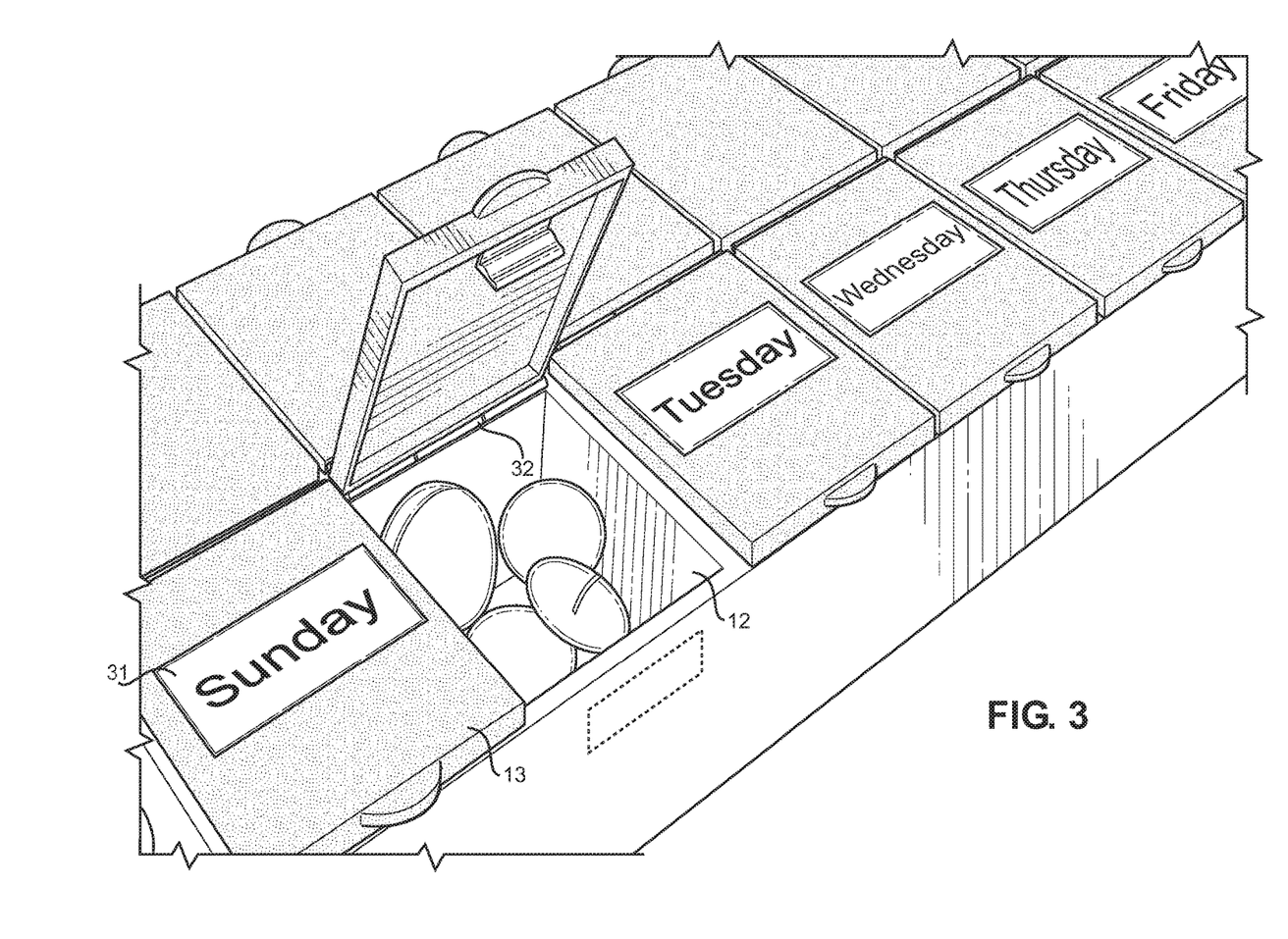
FIG. 3 shows a perspective view of a compartment of the secure pill container.

Referring now to FIG. 3, there is shown a perspective view of the compartments of the secure pill container. In the shown embodiment, indicia 31 (i.e. the names of the days of the week) are represented on the outer surface of the compartment lids 13. In one embodiment, the names of the days of the week may be configured for recognition by an individual with an impairment, including but not limited to a visual impairment, a cognitive impairment, or another impairment. In one embodiment, the names of the days of the week may be visually depicted in any language, including but not limited to English, Spanish, French, Portuguese, Russian, Chinese, Japanese, Korean, a dialect thereof, or another language or dialect thereof. In one embodiment, the names of the days of the week may be communicated in a tactile language, including but not limited to braille.

In one embodiment of the secure pharmaceutical container, each of the lids 13 is connected to its respective compartment 12 by at least one hinge 32 that enables a movement of the lid from the closed position to an open position, and from the open position to the closed position. In one embodiment, each of the lids is connected to its respective compartment by at least one latch that enables a movement of the lid from the closed position to an open position, and from the open position to the closed position.

Figure 4:
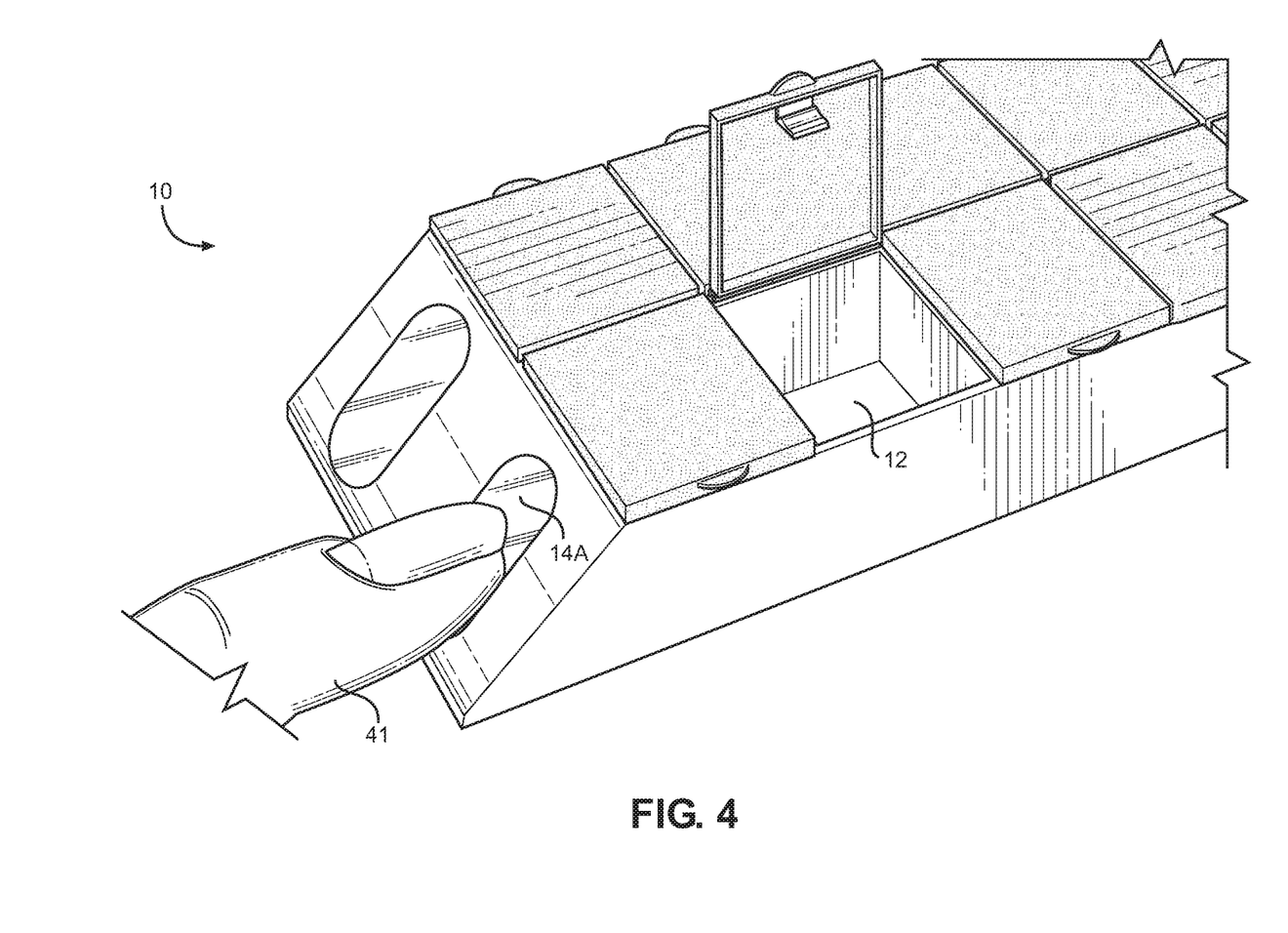
FIG. 4 shows a perspective view of the secure pill container in use.

Referring now to FIG. 4, there is shown a perspective view of the secure pill container in use. The figure depicts a user placing a digit on a fingerprint. In one embodiment, the secure pill container 10 is configured for use by one person. In one embodiment, the secure pill container 10 is configured for use by more than one person. In one embodiment, authentication of a valid user by placement of at least one of the valid user's digits 41 on a fingerprint scanner 14a causes the entire corresponding row of compartments 12 to be unlocked, and the valid user can then choose which compartment to open. In one embodiment, authentication of a valid user by placement of at least one of the user's digits 41 on a fingerprint scanner 14a causes only one of the compartments in the corresponding row to be unlocked, for example, the compartment corresponding to the instant day of the week on the lid (e.g., Monday).

In one embodiment of the secure pharmaceutical container, the first biometric system comprises a first fingerprint scanner attached to a first surface of the housing adjacent to the first row of compartments, and the second biometric system comprises a second fingerprint scanner attached to a second surface of the housing adjacent to the second row of compartments. In one embodiment, the fingerprint scanners are functional without requiring the user to wet their finger with a liquid before applying it to one or more fingerprint scanners. In one embodiment, the first biometric system further comprises a means for validating identity of a user by way of facial recognition, eye feature scanning, voice signature recognition, or a combination thereof. In one embodiment, the second biometric system further comprises a means for validating identity of a user by way of facial recognition, eye feature scanning, voice signature recognition, or a combination thereof. In one embodiment, the first biometric system and the second biometric system each further comprises a means for validating identity of a user by way of facial recognition, eye feature scanning, voice signature recognition, or a combination thereof.

Figure 5:
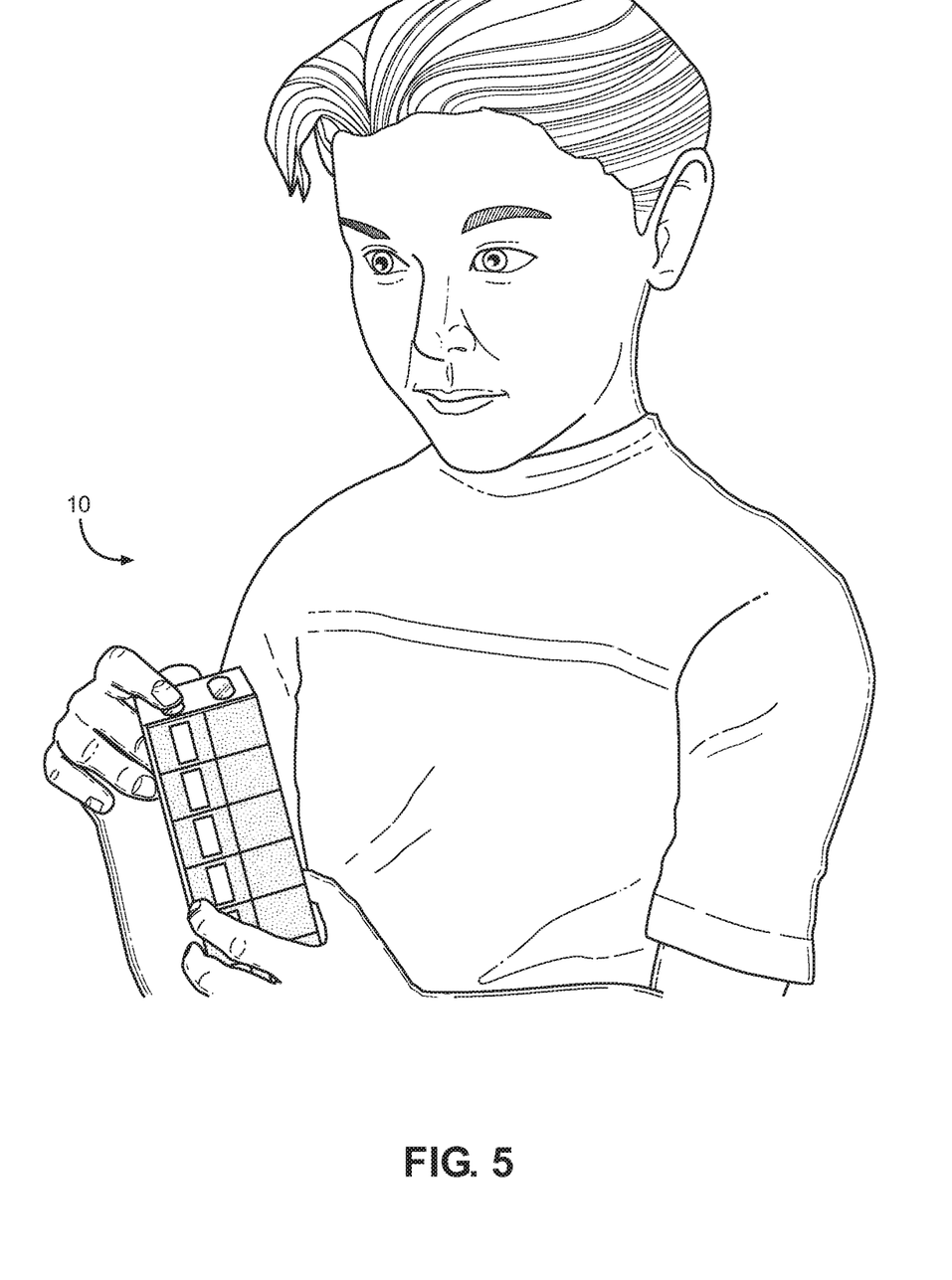
FIG. 5 shows an alternate perspective view of the secure pill container in use.

Referring now to FIG. 5, there is shown an alternate perspective view of the secure pill container in use. The figure depicts a user handling the secure pill container 10 and placing a digit on a fingerprint scanner. In one embodiment, the fingerprint scanner is configured to accept a print of at least one selected from the group including but not limited to: a thumb, a first digit, a second digit, a third digit, a fourth digit, and a combination thereof.

In one embodiment, the secure pharmaceutical container, or related system, further comprises a processor configured to operate the fingerprint scanner. In one embodiment, the secure pharmaceutical container, or related system, further comprises a memory. In one embodiment, the memory may be configured to store one or more approved or authenticated fingerprint scans. In one embodiment, if an individual scans their fingerprint and the scan is not sufficiently identical to an approved or authenticated scan in the memory, the locking mechanism remains locked and the compartments cannot be accessed. In one embodiment, if an individual scans their fingerprint and the scan is sufficiently identical to an approved or authenticated scan in the memory, the locking mechanisms unlock, allowing the individual to access the contents of the individual compartments. In various embodiments, only authorized individuals can access the contents of the secure pharmaceutical container, or related system.

Figure 6:
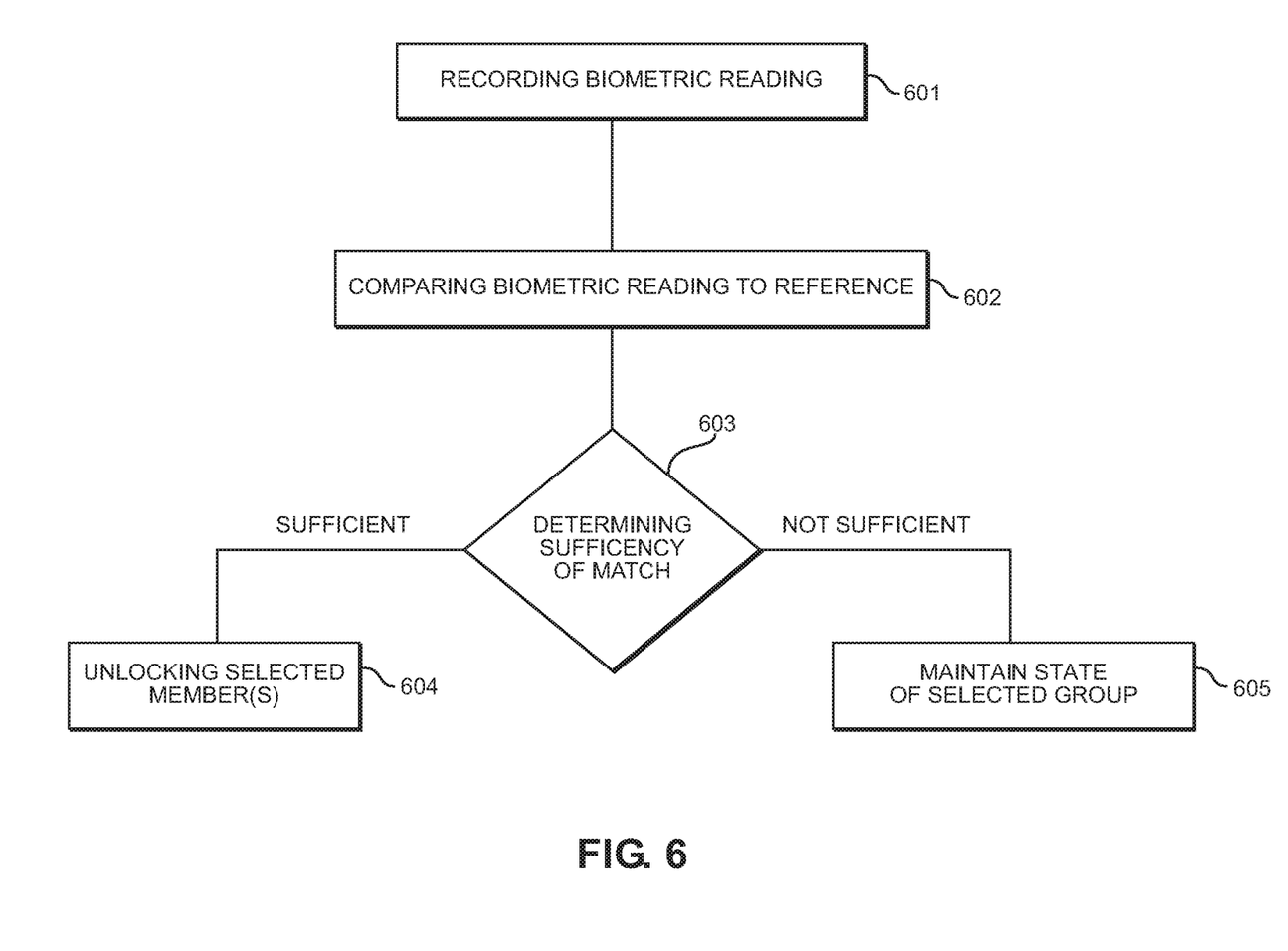
FIG. 6 shows an exemplary flowchart of a method of use of the secure pill container.

Referring now to FIG. 6, there is shown a flowchart of an exemplary method executed by an electronic computing system of the secure pill container. In one embodiment, the housing comprises a first group of compartments wherein each compartment comprises an opening that engages with a lid secured in a closed position by a first locking mechanism, and a second group of compartments wherein each compartment comprises an opening that engages with a lid secured in a closed position by a second locking mechanism. An electronic computing system of the pill container includes a non-transitory computer readable medium, a first biometric system operably connected to the first locking mechanism and configured to actuate the first locking mechanism, and a second biometric system operably connected to the second locking mechanism and configured to actuate the second locking mechanism. A logic is at least partially stored in the non-transitory computer readable medium, which when executed by the electronic computing system, causes the electronic computing system to perform a method, the method comprising: recording a test biometric reading 601, comparing the test biometric reading to a reference biometric reading 602, determining the sufficiency of the biometric reading 603, if determined to be sufficient then unlocking 604 at least one selected from the group consisting of: the first locking mechanism, the second locking mechanism, a portion thereof, and a combination thereof, and if determined to be not sufficient then maintaining the state of the selected group.

In another aspect, the invention provides a secure pharmaceutical container system, comprising: a housing comprising a first group of compartments wherein each compartment comprises an opening that engages with a lid secured in a closed position by a first locking mechanism, and a second group of compartments wherein each compartment comprises an opening that engages with a lid secured in a closed position by a second locking mechanism; an electronic computing system comprising a non-transitory computer readable medium, a first biometric system operably connected to the first locking mechanism and configured to actuate the first locking mechanism, and a second biometric system operably connected to the second locking mechanism and configured to actuate the second locking mechanism; and a logic that is at least partially stored in the non-transitory computer readable medium, which when executed by the electronic computing system, causes the electronic computing system to perform a method, the method comprising: recording a test biometric reading, and comparing the test biometric reading to a reference biometric reading. In one embodiment, the locking mechanisms, operable connections thereof, and actuating configurations thereof are implemented by approaches or standards known in the art.

In one embodiment of the secure pharmaceutical container system, the method further comprises: determining the test biometric reading to be sufficiently identical to the reference biometric reading and unlocking at least one selected from the group including: the first locking mechanism, the second locking mechanism, a portion thereof, and a combination thereof. In one embodiment, the test of sufficiency in identity is accomplished using approaches or standards known in the art.

In one embodiment of the secure pharmaceutical container system, the method further comprises: determining the test biometric reading not to be sufficiently identical to the reference biometric reading. In one embodiment, the test of sufficiency in identity is accomplished using approaches or standards known in the art.

In one embodiment of the secure pharmaceutical container system, the electronic computing system is implemented by at least one selected from the group including: a mobile device, a handheld device, a smartphone, a tablet, a personal computer, and a combination thereof.

In one embodiment of the secure pharmaceutical container system, the electronic computing system comprises at least one biometric functionality selected from the group including: facial recognition, eye feature scanning, fingerprint scanning, voice signature recognition, and a combination thereof.

In one embodiment of the secure pharmaceutical container system, the at least one biometric functionality comprises fingerprint scanning.

In one embodiment of the secure pharmaceutical container system, the system comprises means for wireless communication between the electronic computing system and the housing.

The foregoing descriptions of specific embodiments of the present invention have been presented for purposes of illustration and description. They are not intended to be exhaustive or to limit the present invention to the precise forms disclosed, and modifications and variations are possible in view of the above teaching. The exemplary embodiment was chosen and described to best explain the principles of the present invention and its practical application, to thereby enable others skilled in the art to best utilize the present invention and its embodiments with modifications as suited to the use contemplated.

It is therefore submitted that the instant invention has been shown and described in the most practical and exemplary embodiments. It should be recognized that departures may be made which fall within the scope of the invention. With respect to the description provided herein, it is submitted that the optimal features of the invention include variations in size, materials, shape, form, function and manner of operation, assembly, and use. All structures, functions, and relationships equivalent or essentially equivalent to those disclosed are intended to be encompassed by the present invention.

I claim:
1. A secure pharmaceutical container, comprising:
a housing comprising a first group of compartments wherein each compartment comprises an opening that engages with a lid secured in a closed position by a first locking mechanism, and a second group of compartments wherein each compartment comprises an opening that engages with a lid secured in a closed position by a second locking mechanism;
an electronic computing system comprising a non-transitory computer readable medium, a first biometric system operably connected to the first locking mechanism and configured to actuate the first locking mechanism, and a second biometric system operably connected to the second locking mechanism and configured to actuate the second locking mechanism;

the housing and the electronic computing system are physically connected;

the compartments of the first group of compartments are arranged linearly in a first row, and wherein the compartments of the second group of compartments are arranged linearly in a second row, wherein the first row and the second row are parallel to each other, and wherein the openings and the lids are all on one side of the housing;

the first biometric system comprises a first fingerprint scanner attached to a first surface of the housing adjacent to the first row of compartments;

the second biometric system comprises a second fingerprint scanner attached to a second surface of the housing adjacent to the second row of compartments.

2. The secure pharmaceutical container of claim 1, wherein the first surface and the second surface are adjacent and parallel to each other, and wherein the first surface and the second surface are each part of an angled side of the housing.

3. The secure pharmaceutical container of claim 2, wherein each of the lids is connected to its respective compartment by at least one hinge that enables a movement of the lid from the closed position to an open position, and from the open position to the closed position.

4. A secure pharmaceutical container system, comprising:
a housing comprising a first group of compartments wherein each compartment comprises an opening that engages with a lid secured in a closed position by a first locking mechanism, and a second group of compartments wherein each compartment comprises an opening that engages with a lid secured in a closed position by a second locking mechanism;
an electronic computing system comprising a non-transitory computer readable medium, a first biometric system operably connected to the first locking mechanism and configured to actuate the first locking mechanism, and a second biometric system operably connected to the second locking mechanism and configured to actuate the second locking mechanism;
a logic that is at least partially stored in the non-transitory computer readable medium, which when executed by the electronic computing system, causes the electronic computing system to perform a method, the method comprising:
recording a test biometric reading;
comparing the test biometric reading to a reference biometric reading;

the housing and the electronic computing system are physically connected;
the compartments of the first group of compartments are arranged linearly in a first row, and wherein the compartments of the second group of compartments are arranged linearly in a second row;
the first row and the second row are parallel to each other, and wherein the openings and the lids are all on one side of the housing;
the first biometric system comprises a first fingerprint scanner attached to a first surface of the housing adjacent to the first row of compartments;
the second biometric system comprises a second fingerprint scanner attached to a second surface of the housing adjacent to the second row of compartments.

5. The secure pharmaceutical container system of claim 4, wherein the method further comprises:
determining the test biometric reading to be sufficiently identical to the reference biometric reading,
unlocking at least one selected from the group consisting of: the first locking mechanism, the second locking mechanism, a portion thereof, and a combination thereof.

6. The secure pharmaceutical container system of claim 4, wherein the method further comprises:
determining the test biometric reading not to be sufficiently identical to the reference biometric reading.

7. The secure pharmaceutical container system of claim 4, wherein the first surface and the second surface are adjacent and parallel to each other, and wherein the first surface and the second surface are each part of an angled side of the housing.

8. The secure pharmaceutical container system of claim 7, wherein each of the lids is connected to its respective compartment by at least one hinge that enables a movement of the lid from the closed position to an open position, and from the open position to the closed position.

9. The secure pharmaceutical container system of claim 4, wherein the electronic computing system is implemented by at least one selected from the group consisting of: a mobile device, a handheld device, a smartphone, a tablet, a personal computer, and a combination thereof.

10. The secure pharmaceutical container system of claim 9, wherein the electronic computing system comprises at least one biometric functionality selected from the group consisting of: facial recognition, eye feature scanning, fingerprint scanning, voice signature recognition, and a combination thereof.

11. The secure pharmaceutical container system of claim 10, wherein the system comprises means for wireless communication between the electronic computing system and the housing.

* * * * *